US010159556B2

(12) United States Patent
McGuckin, Jr. et al.

(10) Patent No.: US 10,159,556 B2
(45) Date of Patent: Dec. 25, 2018

(54) METHOD OF INSERTING A VEIN FILTER

(71) Applicant: Argon Medical Devices, Inc., Plano, TX (US)

(72) Inventors: James F. McGuckin, Jr., Radnor, PA (US); James Erich Bressler, Langhorne, PA (US); John D. Leedle, Philadelphia, PA (US); Colin Valentis, Penndel, PA (US)

(73) Assignee: Argon Medical Devices, Inc., Plano, TX (US)

( * ) Notice: Subject to any disclaimer, the term of this patent is extended or adjusted under 35 U.S.C. 154(b) by 308 days.

(21) Appl. No.: 14/678,938

(22) Filed: Apr. 4, 2015

(65) Prior Publication Data
US 2015/0313702 A1 Nov. 5, 2015

Related U.S. Application Data

(60) Provisional application No. 61/988,051, filed on May 2, 2014.

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2230/005* (2013.01)

(58) Field of Classification Search
CPC ................. A61F 2/01; A61F 2230/005; A61F 2002/011; A61F 2002/016
See application file for complete search history.

(56) References Cited

U.S. PATENT DOCUMENTS

| | | | |
|---|---|---|---|
| 2005/0101982 A1 | 5/2005 | Ravenscroft et al. | |
| 2005/0222604 A1* | 10/2005 | Schaeffer | A61F 2/01 606/200 |
| 2006/0106417 A1* | 5/2006 | Tessmer | A61F 2/01 606/200 |
| 2009/0318951 A1 | 12/2009 | Kashkarov et al. | |
| 2011/0313503 A1* | 12/2011 | Berra | A61F 2/07 623/1.11 |

FOREIGN PATENT DOCUMENTS

| | | |
|---|---|---|
| EP | 2628463 A1 | 8/2013 |
| FR | 2945440 A1 | 11/2010 |

OTHER PUBLICATIONS

Search Report by the European Patent Office, European patent application No. 15166102.2, Date of Search: Oct. 1, 2015.

* cited by examiner

*Primary Examiner* — Julie A Szpira
(74) *Attorney, Agent, or Firm* — IpHorgan Ltd.

(57) ABSTRACT

A method of implanting a vessel filter by a femoral approach comprising the steps of providing a sheath with a pusher and the vessel filter positioned therein and providing a sheath centering structure movable within the sheath. The centering structure has a distal portion expandable from a collapsed position within the sheath to an expanded position outside the sheath. The steps further include inserting the sheath into the vessel, moving the centering structure with respect to the sheath to enable the centering structure to move from the collapsed position to the expanded position to move a distal tip of the sheath away from a vessel wall and to a more centered position, and subsequently exposing the vessel filter from the sheath to enable the filter to move from a collapsed position to an expanded position. An implantation system is also provided.

8 Claims, 16 Drawing Sheets

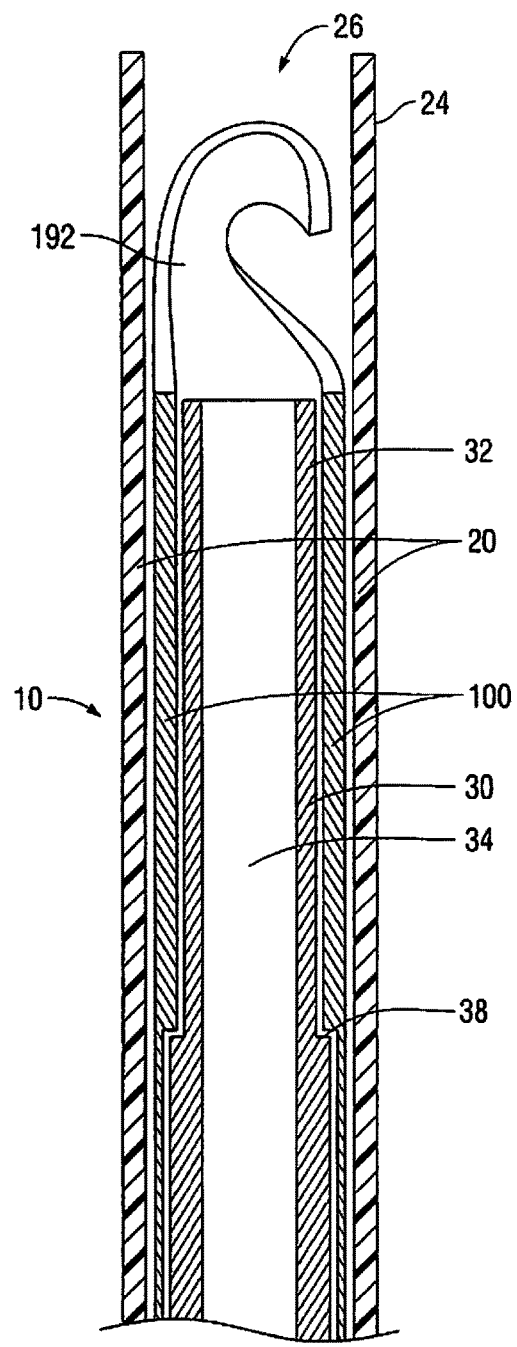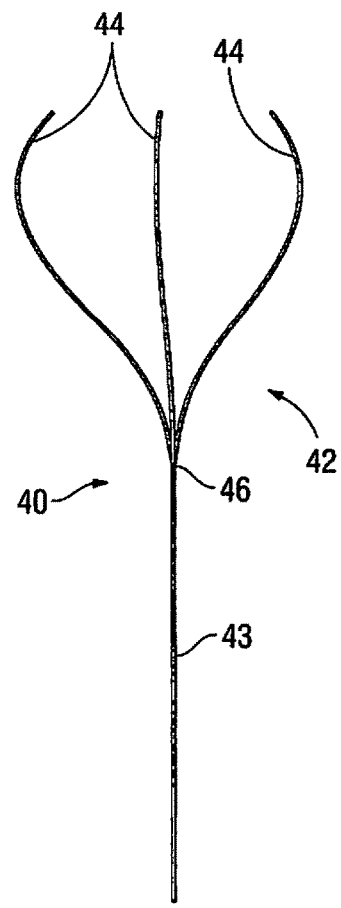
FIG. 5A
FIG. 5B

METHOD OF INSERTING A VEIN FILTER

PRIORITY CLAIM

This application claims priority from provisional application Ser. No. 61/988,051, filed on May 2, 2014, the entire contents of which are incorporated herein by reference.

BACKGROUND

Technical Field

This application relates to a vascular filter and more particularly to a method of inserting a vein filter into the vessel.

Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

To avoid invasive surgery, less invasive surgical techniques involving placement of a mechanical barrier in the inferior vena cava have been developed. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Commonly assigned U.S. Pat. No. 7,704,266 (the "266 patent") and U.S. Pat. No. 8,162,972 (the "972 patent"), the entire contents of both of which are incorporated herein by reference, disclose other forms of vein filters. These filters can be permanently implanted or removed minimally invasively, e.g. intravascularly.

The methods of placement of the filter described in the '274 and '972 patents are effective. However, in certain patients, the vena cava is not straight, but is curved and/or more tortuous. Although the filters of the '274 patent and '972 patents can be placed effectively in such vena cava, it would be advantageous to provide a delivery method and apparatus to even better accommodate these curved anatomies.

Additionally, the better centered the filter, the easier the subsequent removal of the filter. This is due to the fact that if the retrieval end (cranial end) of the filter is against the vessel wall when placed, access to the retrieval end could be difficult. Also, additional tissue ingrowth could occur over the cranial end which could increase the difficulty of removal.

Prior art attempts to center the filter include modifications to the filter itself to provide centering structure. Not only does this complicate the filter design but could require the length of the filter to be increased. Such increased length can be disadvantageous due to limited space in the inferior vena cava.

Commonly assigned Patent Publication No. 2009/0143813 (Ser. No. 12/288,217, filed Oct. 17, 2008) discloses an attempt to center the filter without modifying the filter. In this patent publication, the delivery system is modified to provide for more centered placement of the filter by moving the delivery sheath opening toward a center of the vessel by use of a curved pusher. Although in certain applications this method has been effective, sometimes the user does not properly perform the technique and therefore the filter is not centered upon delivery.

Therefore, it would be advantageous to improve centered delivery of a filter within the vessel by modifications of the filter delivery system, rather than the filter itself, and which can provide a more reliable and consistent technique for centered placement.

SUMMARY

The present invention provides a method of implanting a vein filter to facilitate centering of the filter at the surgical site. The present invention also provides a method of delivering the filter in a manner to facilitate later removal of the filter from the vessel. This is achieved by providing an expandable centering member as part of the delivery system which is preferably movable with respect to the pusher utilized for deploying the filter in the vessel.

In one aspect, the present invention provides a method of implanting a vessel filter in a vessel by a femoral approach comprising the steps of:

providing a sheath having a distal tip and having a filter pusher and vessel filter positioned therein;

providing a sheath centering structure within the sheath and movable with respect to the sheath, the centering structure having a distal portion expandable from a collapsed position within the sheath to an expanded position outside the sheath;

inserting the sheath into the vessel;

moving the centering structure with respect to the sheath to enable the centering structure to move from the collapsed position to the expanded position to move the distal tip of the sheath away from a vessel wall and to a more centered position within the vessel; and subsequently exposing the vessel filter from the sheath to enable the filter to move from a collapsed condition to an expanded condition within the vessel.

In some embodiments, the method includes the step of advancing the sheath through the femoral vein into the vena cava.

In some embodiments, the pusher includes a lumen extending therein, and the centering structure includes a wire, the wire movable within the lumen of the pusher and through the filter. The pusher can have a stepped portion forming a shoulder to support the filter and the vessel filter can be mounted on the pusher within the sheath.

In some embodiments, the centering structure includes a plurality of wires extending from an apex and terminating in free ends; in other embodiments, the centering structure includes a plurality of wires extending from an apex and joined at terminal ends. In some embodiments, the centering structure includes a plurality of wires bowing radially outwardly in the expanded configuration.

In some embodiments, the step of subsequently exposing the filter includes the step of moving the pusher and/or sheath relative to each other.

The method can further include the step of removing the vein filter from the vessel.

In accordance with another aspect, an implantation system for a vascular implant is provided comprising a sheath having a longitudinal axis, a lumen formed therein and a distal opening. A pusher is positioned within the sheath in contact with the vascular implant to deliver the implant from the sheath, the implant moving from a reduced profile position within the sheath to an expanded placement position when exposed from the sheath. The implant is configured for deployment through the distal opening in the sheath for implantation in a patient's body. A centering structure includes an elongated portion and a plurality of arms extending from a distal portion of the elongated portion, the arms movable from a reduced profile position to an expanded position to move the sheath away from the vessel wall to a more centered position, and the centering structure is movable relative to the pusher.

In some embodiments, the pusher comprises a lumen and the centering structure is slidably positioned within the pusher. In some embodiments, the pusher includes a stepped portion forming a shoulder to support the implant.

Preferably, the centering structure is movable independent of the pusher and is movable through the implant.

In some embodiments, the arms of the centering structure are joined at an apex and terminate in free ends; in other embodiments, the arms are joined at proximal and distal ends to form a basket like structure.

In some embodiments, the implant comprises a vessel filter, the filter moving to the expanded position when deployed from the sheath.

In accordance with another aspect, the present invention provides in combination, a delivery sheath, a filter, a pusher and a centering structure. The delivery sheath has a lumen therein dimensioned to receive the filter, the filter positioned within the sheath and configured for deployment through a distal opening in the sheath for implantation in a patient's body. The pusher is slidably positioned with respect to the sheath and engages the filter for deployment of the filter from the sheath. The centering structure is slidably positioned with respect to the filter, pusher and sheath, and has an expandable distal portion to aid centering of the sheath and thus centering of the filter upon delivery of the filter from the delivery sheath.

In some embodiments, the centering structure is slidable within a lumen of the pusher.

BRIEF DESCRIPTION OF THE DRAWINGS

Preferred embodiment(s) of the present disclosure are described herein with reference to the drawings wherein:

FIG. 5A is an enlarged longitudinal cross-sectional view taken along line 5A-5A of FIG. 5;

FIG. 5B is a perspective view of the centering structure of FIG. 5:

DETAILED DESCRIPTION OF PREFERRED EMBODIMENTS

Figure 1:
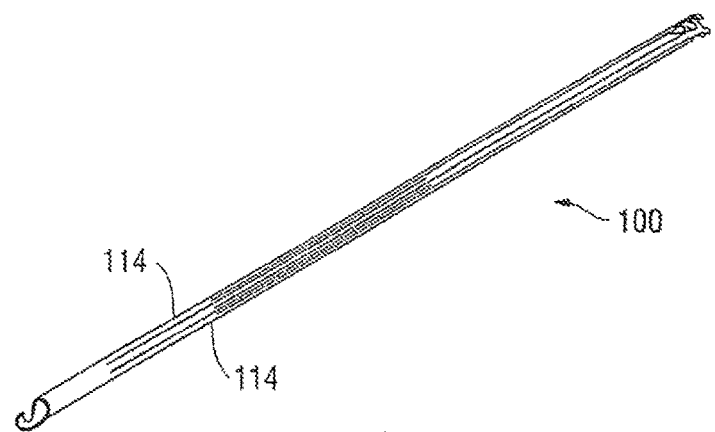
FIG. 1 is a perspective view of one embodiment of a filter shown in a collapsed delivery position.

Turning now to the drawings, wherein like reference numerals identify similar or like components throughout the several views, a method of implanting vein filters is disclosed. The filter is inserted via a femoral approach. In commonly assigned U.S. Pat. Nos. 7,704,266 and 8,162,972, the entire contents of each of which are incorporated herein by reference, various embodiments of filters are described with various structures. The delivery system of the present invention can be used to insert the filters disclosed in these patents as well as used to insert other filters.

As is common, the term "proximal" used herein refers to the part closer to the user, e.g., surgeon, and the term "distal" refers to the part further from the user. Thus, for example, the distal opening of the delivery sheath is the part further from the user as the proximal end extends from the patient's body for manipulation by the user.

Figure 5:
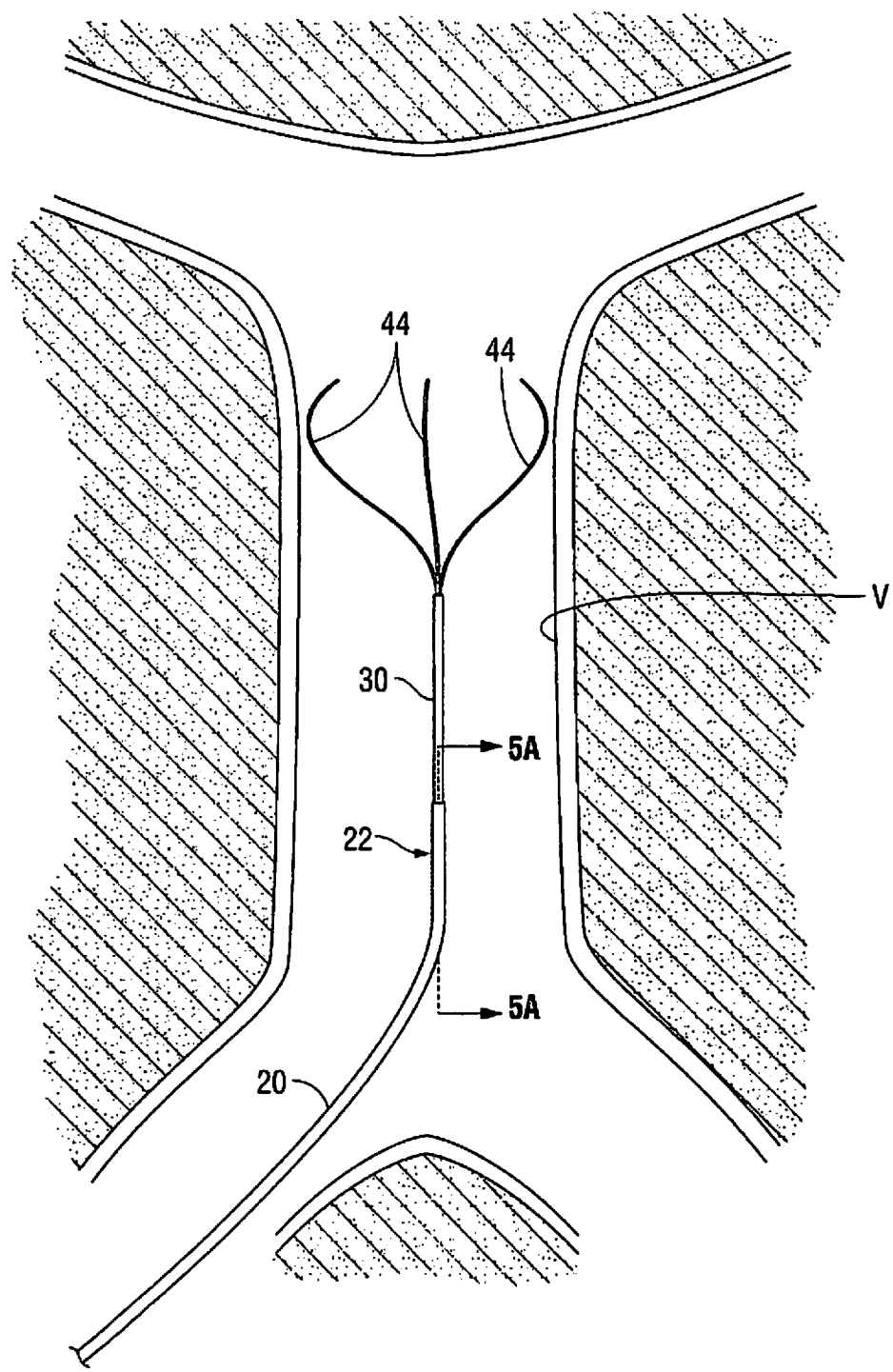
FIG. 5 is a side view illustrating the centering wires of a first embodiment of the centering structure of the present invention, the centering structure exposed from the delivery sheath to center the distal opening of the delivery catheter.
Figure 6:
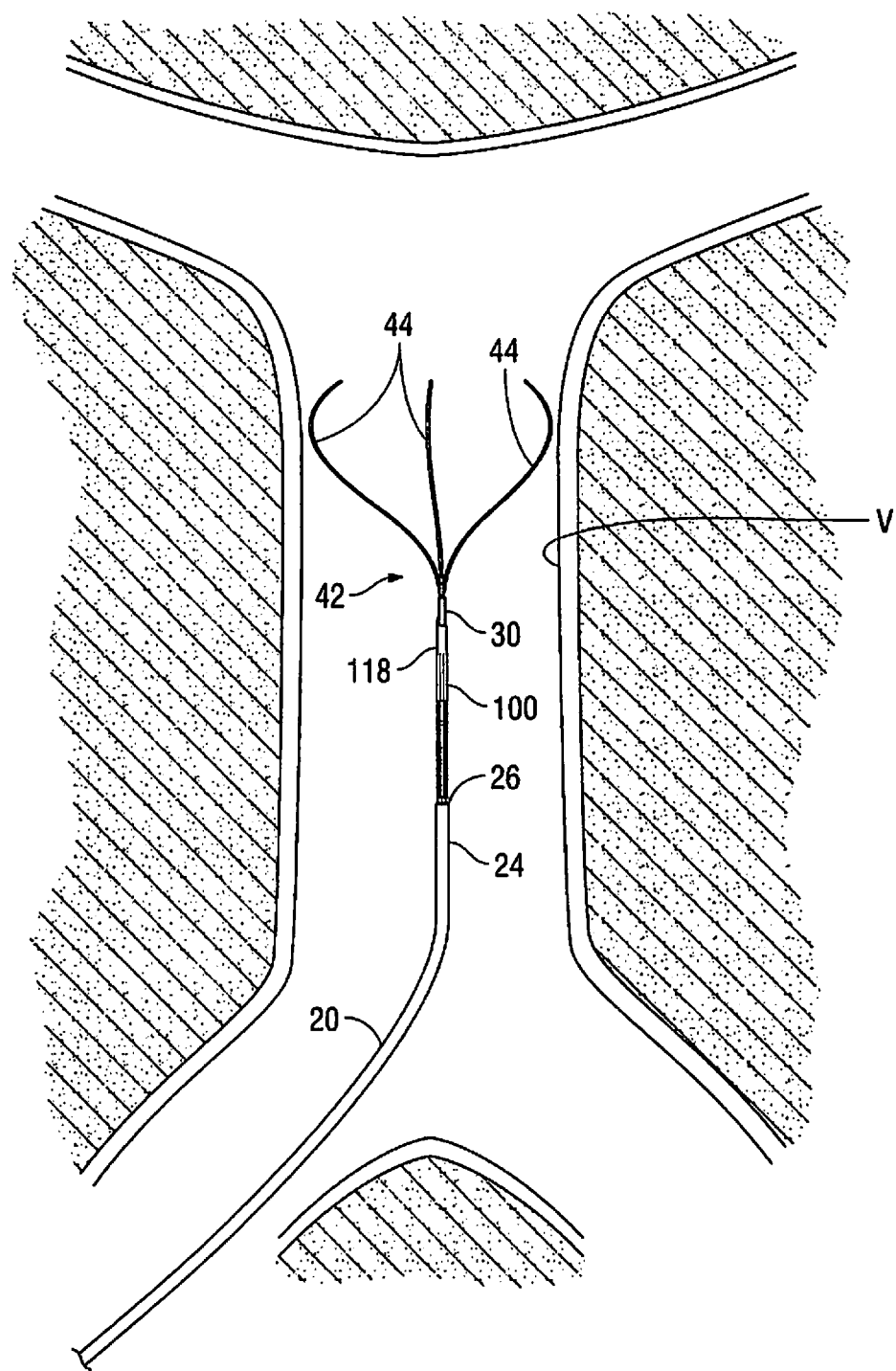
FIG. 6 is a side view similar to FIG. 5 showing the filter partially exposed from the delivery sheath but not yet expanded.
Figure 7A:
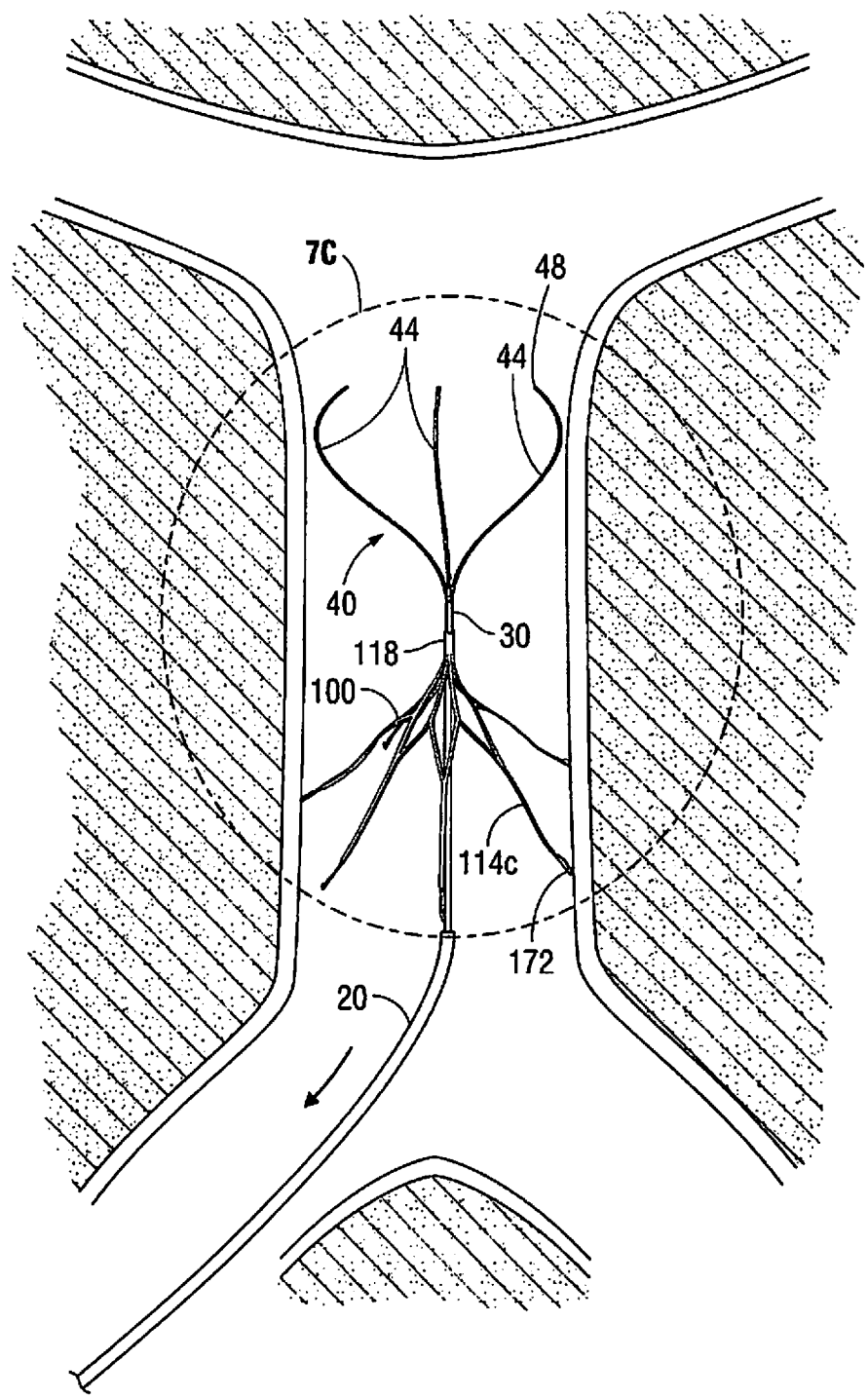
FIG. 7A is a side view similar to FIG. 6 illustrating the filter fully deployed from the delivery sheath and in the expanded position.
Figure 7B:
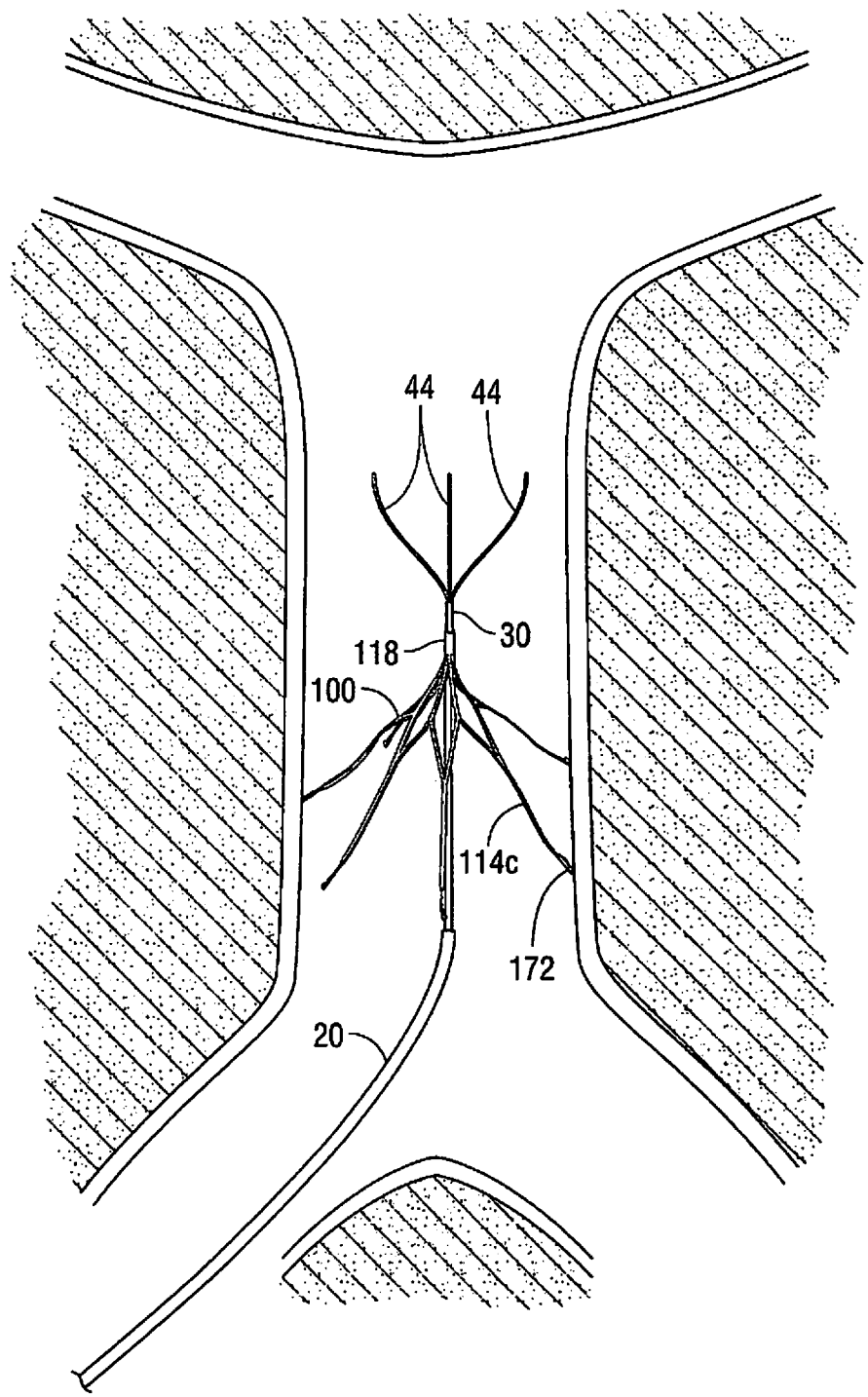
FIG. 7B is a view similar to FIG. 7A showing partial withdrawal of the centering wires into the filter pusher after full deployment of the filter.

Turning initially to FIGS. 5A and 7A, the filter delivery system 10 of the present invention has a delivery catheter or sheath 20 forming the outermost tube, a filter pusher 30 and a centering structure or centering mechanism 40 (or 140). For clarity, the centering structure 40 is not shown in FIG. 5A.

Figure 3:
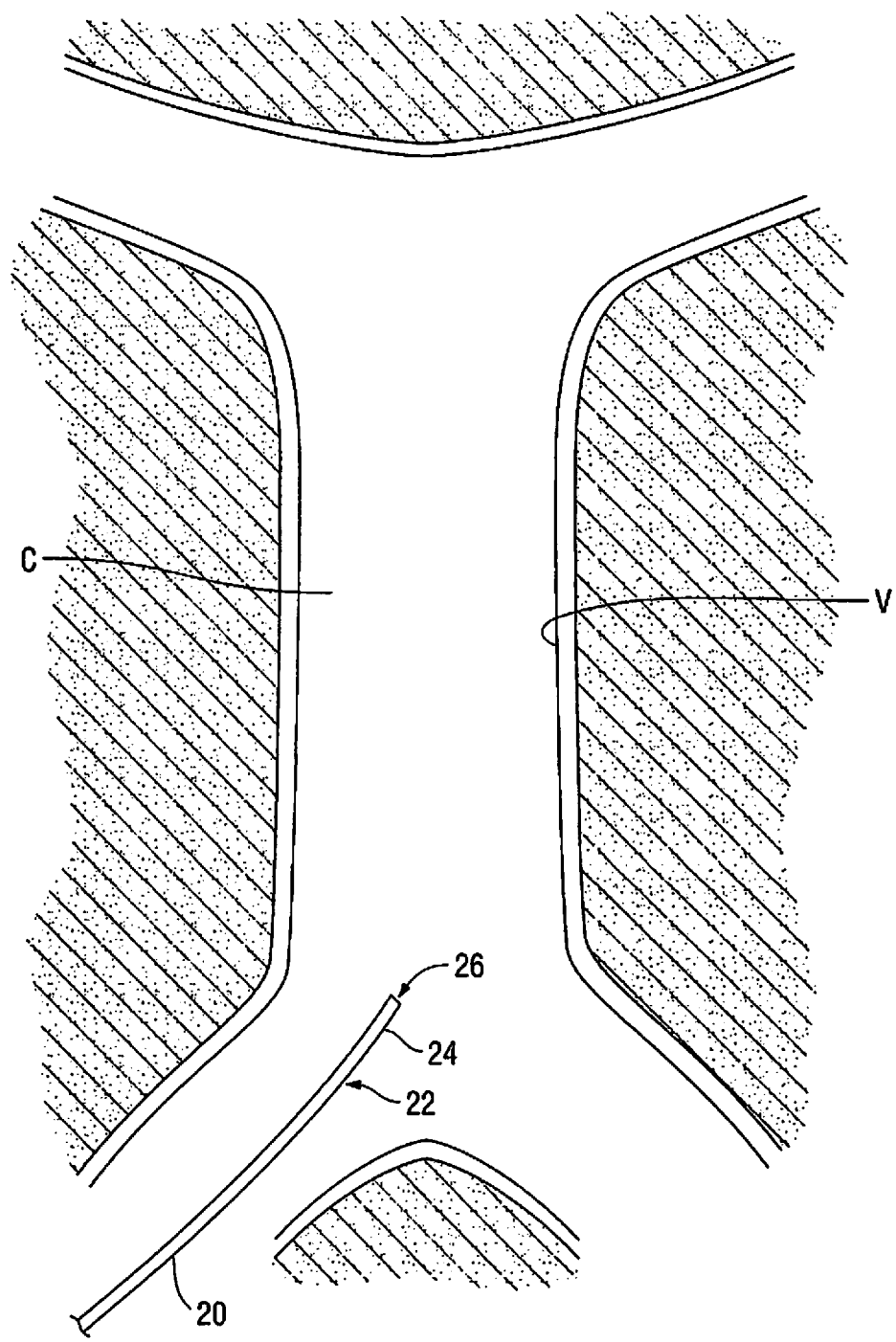
FIG. 3 is a side view of the delivery sheath (catheter) being inserted into the vena cava of a patient (via a femoral approach)

Delivery sheath (catheter) 20 has a distal tip 24 and a distal opening 26 at distal portion 22 (FIG. 3). In a preferred embodiment, the sheath 20 can be composed of a Pebax material with a stainless steel braid embedded in the wall to increase its rigidity. A PTFE liner or coating is preferably provided on the inner surface of the sheath. Other materials and compositions are also contemplated. The sheath can have a hub (not shown) at a proximal portion for connection of a tube to allow for injection of cold saline, if desired, as described in the '266 patent which can be provided to maintain the filter in a relatively softer condition as it is in the martensitic state within the sheath. The tubing can also be utilized to inject other fluids.

The filter pusher 30 has a distal tip 32 and a lumen 34 extending therethrough (see FIG. 5A). At a distal portion, but spaced proximally from the distal tip 32, a step is formed to create a shoulder 38 to abut and support a filter thereon. The pusher 30 is in contact with the filter 100 by the abutment of the shoulder 38 and filter and deploys the filter 100 either by distal movement of the pusher 30 to advance the filter 100 from the sheath 20, by proximal movement of the sheath 20 to expose the filter 100, or by movement of both the pusher 30 distally and the sheath 20 proximally. In either event, such relative movement of the pusher 30 and sheath 20 exposes the filter 100 so it can move from its collapsed reduced profile delivery position or condition (see FIG. 1) contained with the sheath 20 to its expanded position or condition (FIGS. 2 and 7A) exposed from the sheath 20 to contact the vessel wall.

The pusher 30 can be formed from a tube. In a preferred embodiment, the pusher 30 can be formed of Pebax material. The centering wires can be composed of stainless steel. Other materials and compositions of the pusher and wires are contemplated. A wire protruding beyond the distal end of the pusher 30 also can serve as a guidewire. The wire can also help keep the vessel engaging hooks of the filter separated during insertion. A marker band or other indicia can be provided to provide a visual indication of when the filter is at the distal end of the sheath (when the markings are adjacent a proximal end of a filter cartridge). Note in some embodiments, the centering wire can be attached to a hub of the pusher for slidable movement, e.g., by a control knob, such as in the embodiment described below.

The centering structure is designated by generally by reference numeral 40 and has a distal portion 42 and a proximal portion extending outside the body for manipulation by the user. Distal portion 42 includes a plurality of centering arms 44, joined at apex 46, bowing radially outwardly and terminating in free ends 48 (FIGS. 5B and 7A). In a preferred embodiment, three centering arms 44 are provided, however, a fewer or greater number of arms can alternatively be provided. The centering structure 40 is slidably positioned within lumen 34 of the filter pusher 30 and therefore moves, e.g., slides, relative to the pusher 30, sheath 20 and filter 100. That is, the centering structure 40 is movable from a retracted (collapsed) position within the delivery sheath 20 to an extended (advanced) position where the distal portion 42 extends beyond the distal tip 24 of sheath 20 for movement from a collapsed to an expanded position.

In one embodiment, the centering structure 40 is formed by a series of wires, e.g., an elongated wire 43 with centering arms 44 formed of separate wires and attached to a distal portion of the wire 43 at apex 46 such as by welding, crimping, soldering, bonding or other known methods. Alternatively, the elongated wire 43 can form one of the centering arms and then additional centering arms 44 can be attached to a region of the elongated wire 43 slightly proximal of its distal tip (as in the location of apex 46). The centering structure can alternatively be formed integrally from a monolithic wire or hypotube. The one piece structure can be laser cut and shape set.

The wires of the centering structure can be made of shape memory material such as Nitinol. In this manner, the wires are collapsed into a low profile position where the arms 44 are substantially aligned with a longitudinal axis of the delivery sheath 20 for delivery. When advanced from the sheath 20, the centering wires are exposed and return to their shape memorized expanded configuration (position) of FIG. 5. Alternatively, they can be composed of spring material such as, stainless steel, and biased to an expanded position. Additionally, as an alternative, the centering wires could be moved to an expanded position when exposed from the sheath by an actuating mechanism, e.g., by actuating a wire or cable which when pulled bows the arms 44.

Note in the expanded position, the apex 46 can be exposed; alternatively the apex 46 can remain within the confines of the sheath 20 or pusher 30.

As shown, when the centering wires expand, they have a transverse dimension sufficiently large to contact, preferentially circumferentially, the wall of the vessel, thereby keeping the delivery sheath 20 and distal tip 32 of the pusher 30 substantially centered within the vessel. It should be appreciated that the term "substantially centered" as used herein includes exactly centered within the vessel as well as slightly off center such as at an angle of up to about 30 degrees with respect to the longitudinal axis of the vessel, but preferably smaller. By keeping this angle closer to zero, centering of the delivery sheath distal tip 24 and distal opening 26, and therefore the filter 100 when delivered, can better be achieved.

Figure 9:
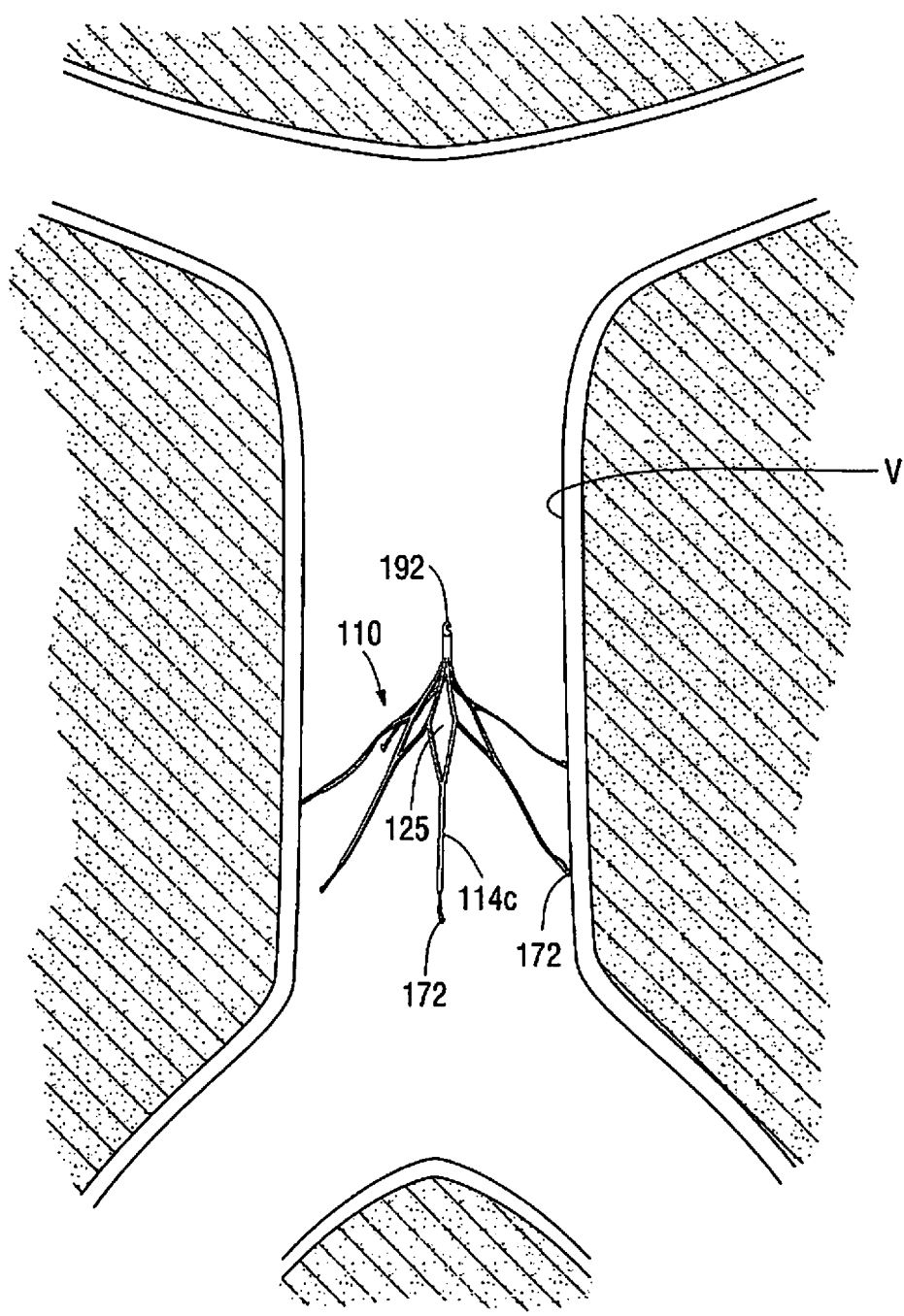
FIG. 9 is a side view similar to FIG. 8 illustrating the delivery sheath withdrawn and the filter substantially centered in the vessel in an expanded position.
Figure 10A:
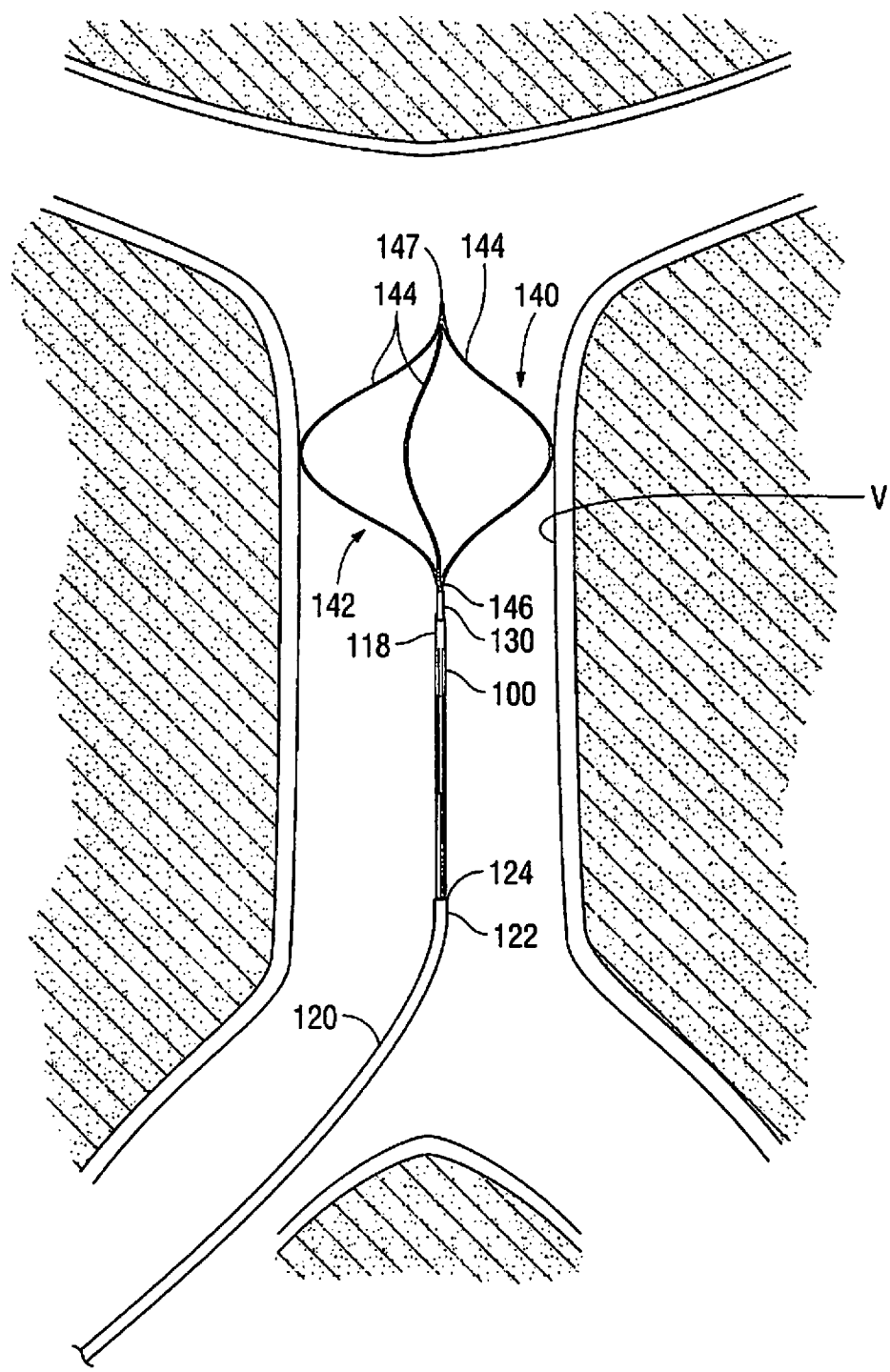
FIG. 10A is a side view similar to FIG. 6 illustrating an alternate embodiment of a centering structure of the present invention in the form of a basket, the centering structure shown in the expanded configuration and the filter show partially exposed from the delivery sheath but not yet expanded.
Figure 10B:
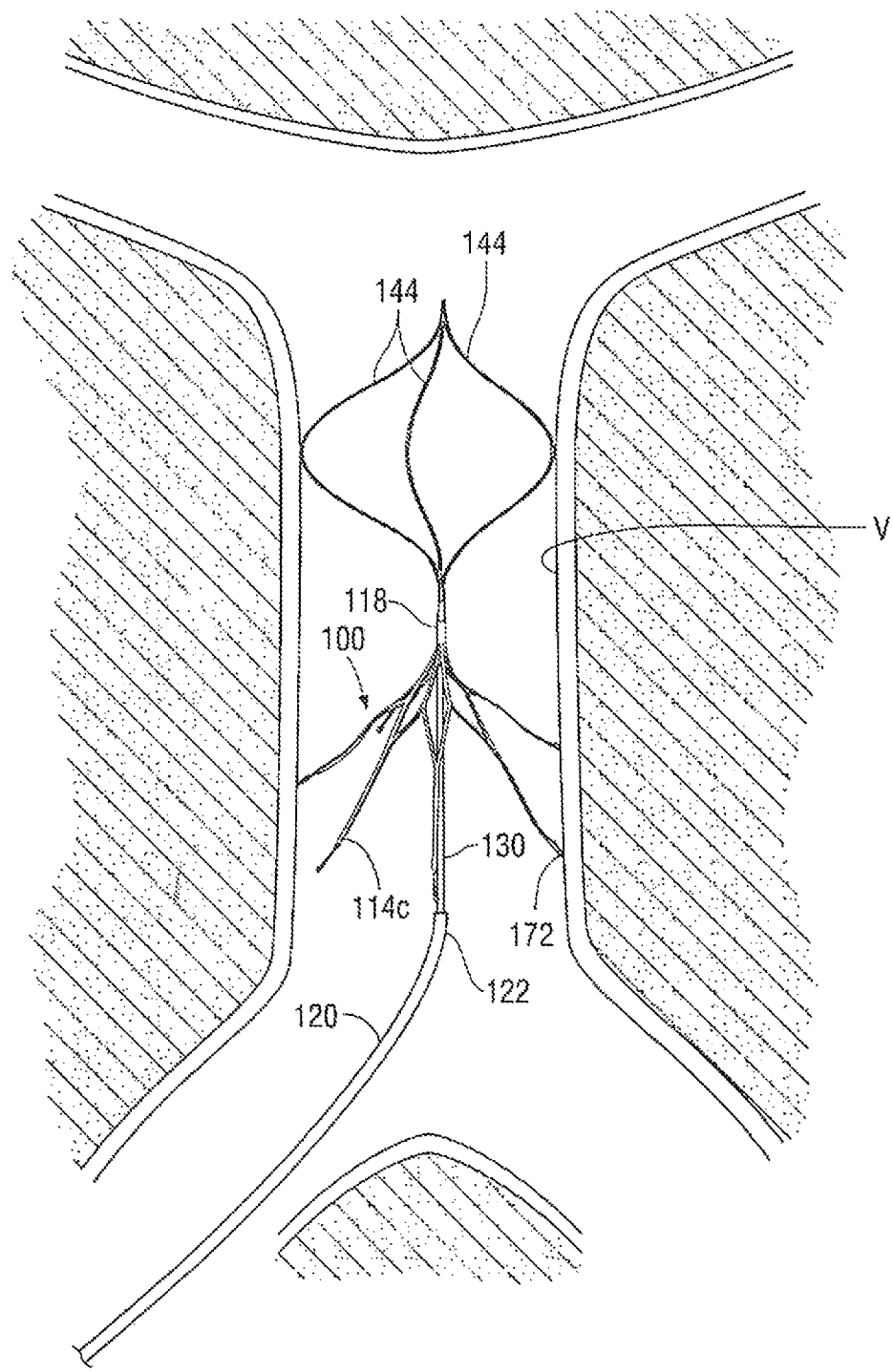
FIG. 10B is a side view similar to FIG. 10A showing the filter fully deployed from the delivery sheath and in the expanded position.
Figure 10C:
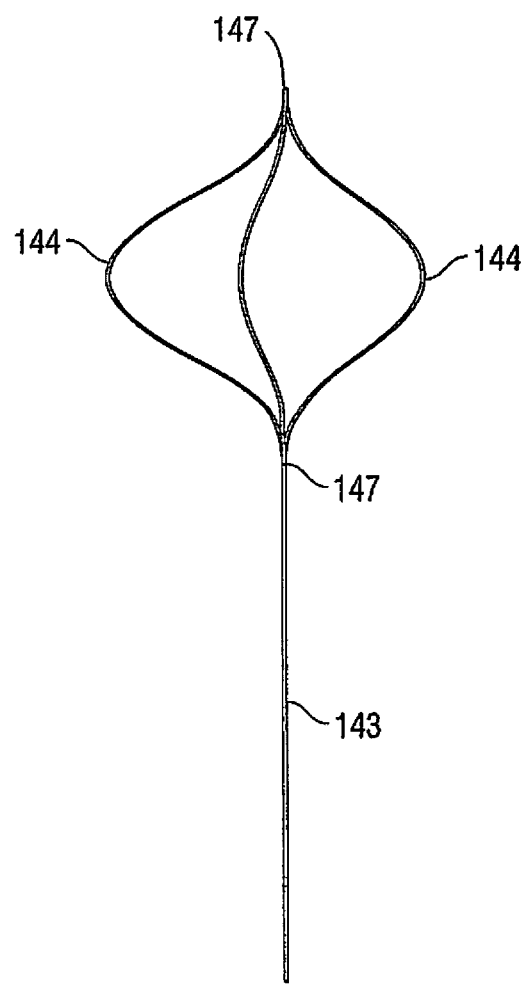
FIG. 10C is a perspective view of the centering structure of FIG. 10A.

An alternate embodiment of the centering structure is illustrated in FIGS. 10A-10C. The delivery sheath and filter pusher of FIG. 10A are identical to that of the embodiment of FIGS. 1-9, and therefore for brevity are not described in detail again. In short, filter pusher 130 is identical to filter pusher 30 and includes a distal tip and a shoulder (not shown) identical to shoulder 38. Delivery sheath or catheter 120 is identical to delivery sheath 20 and includes a distal tip 122 and a distal opening 124 for exit of the filter 100, identical to distal tip 22 and opening 24 of delivery sheath 20.

Centering structure 140 differs from centering structure 40 in that it is a closed loop design. More specifically, distal portion 142 includes a plurality of centering arms 144, joined at proximal apex 146 and at distal converging region 147. The connection at distal region 147 provides more structural integrity. Centering arms 144 bow radially outwardly between their proximal and distal fixed points. In a preferred embodiment, three centering arms 144 are provided, however, a fewer or greater number of arms can alternatively be provided. The centering structure 140 is slidably positioned within a lumen of the filter pusher 130 (similar to lumen 34 of pusher 30) and therefore moves, e.g., slides, relative to the pusher 130, sheath 120 and filter 100. That is, the centering structure 140 is movable from a retracted position within the delivery sheath 120 to an extended (advanced) or exposed position where it extends beyond the distal tip of sheath 120 for movement from a collapsed position to the expanded position of FIGS. 10A and 10B.

In one embodiment, the centering structure is formed by a series of wires, e.g., an elongated wire 143 (FIG. 10C) with centering arms 144 formed of separate wires and attached to a distal portion of the wire 143 at apex 146 such as by welding, crimping, soldering, bonding or other known methods. The arms 144 are also attached at distal converging region 147 by welding, crimping, bonding, soldering or other known methods. Alternatively, the elongated wire 143 can form one of the centering arms and then additional centering arms 144 are attached to a region of the elongated wire 143 slightly proximal of the distal tip (as in the location of apex 146) and at the distal tips (as in distal region 147). The centering structure 140 can alternatively be formed integrally from a monolithic wire or hypotube. The one piece structure can be laser cut and shape set.

The wires of the centering structure can be made of shape memory material. In this manner, the wires are collapsed into a low profile position where the arms 144 are substantially aligned with a longitudinal axis of the delivery sheath 120 for delivery. When advanced from the sheath 120, the wires are exposed and return to their shape memorized expanded configuration (position) of FIGS. 10A and 10B. Alternately, they can be composed of spring material such as stainless steel, and biased to an expanded position. Note in the expanded position, the proximal apex 146 can be exposed; alternatively the apex 146 can remain within the confines of the sheath 120 or pusher 130. An actuation mechanism, e.g., a wire or cable, can alternatively be used, e.g., pulled, to bow the arms 144 when exposed.

As shown, when the wires expand, the have a transverse dimension sufficiently large to contact the wall of the vessel, thereby keeping the delivery sheath 120 and distal tip 122 of pusher 120 substantially centered within the vessel. Substantially centered as noted above includes exactly centered as well as slightly off center such as at an angle of up to 30 degrees with respect to the longitudinal axis, but preferably smaller. By keeping this angle closer to zero, centering of the opening of the delivery sheath 120, and therefore the filter 100 when delivered, can better be achieved.

FIGS. 11A-12B illustrate alternate embodiments wherein the centering structure is attached to the pusher. In the foregoing embodiments, the centering mechanism is unattached to the pusher and slid within a lumen of the pusher. In the embodiments of FIGS. 11A-12B the centering mechanism is attached at a proximal end to the pusher and is slid within the lumen of the pusher between retracted and advanced positions.

Figure 11A:
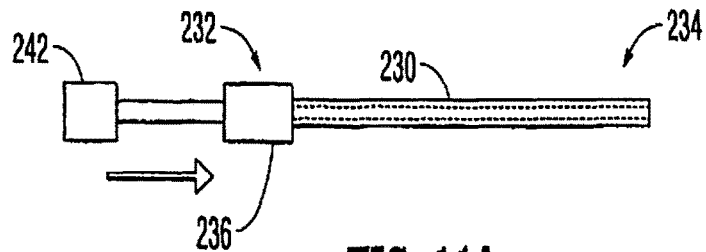
FIG. 11A is a perspective view of an alternate embodiment of the pusher and centering mechanism of the present invention, the centering mechanism shown in the retracted position.
Figure 11B:
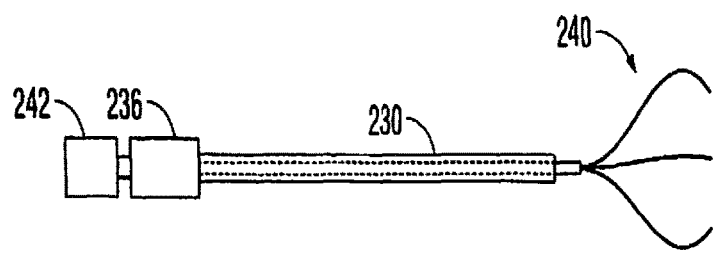
FIG. 11B is a view similar to FIG. 11A showing the centering mechanism advanced from the pusher.

Turning to the embodiment of FIGS. 11A and 11B, filter pusher 230 has a proximal portion 232 and a distal portion 234. A centering mechanism 240 is slidingly received within a lumen of the pusher 230 for movement between a retracted position wherein the distal portion of the centering structure 240 is contained within the confines of the pusher 230 in a collapsed position and an extended exposed position (FIG. 11B) wherein the distal portion of the centering structure 240 is exposed from the pusher 230 to move to the expanded position. The centering structure 240 shown includes a series of wires with free ends as in the embodiment of FIG. 5. Alternatively, the centering structure can be in the form of a basket or closed loop as in the structure of FIG. 10A. Hub or handle 242 of centering mechanism 240 is grasped by the user and moved toward the hub or handle 236 of filter pusher 230 to advance the centering structure 240 with respect to the pusher 230 and sheath within which the pusher 230 is located. The centering wires are thereby slidably attached to the pusher 230, for example, within a plurality of channel guides in hub 236, each dimensioned to receive one of the centering wires. Alternatively, a single channel guide can be provided to receive only one of the centering wires, e.g., the central wire. In either event, the centering mechanism is attached (connected) to the pusher mechanism for slidable movement therein.

Figure 12A:
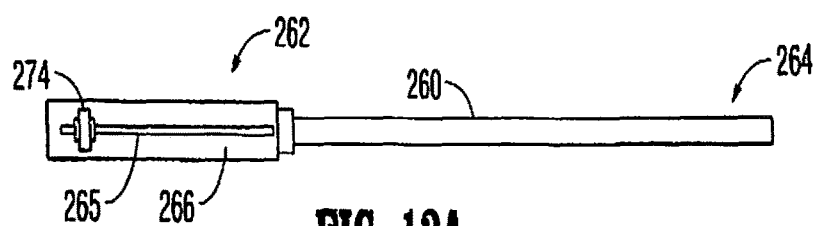
FIG. 12A is a perspective view of another alternate embodiment of the pusher and centering mechanism of the present invention, the centering mechanism shown in the retracted position.
Figure 12B:
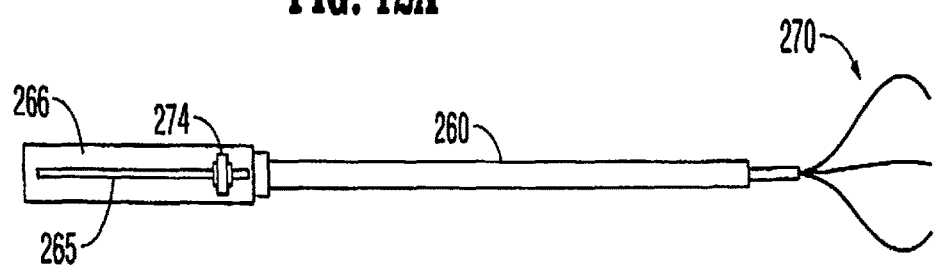
FIG. 12B is a view similar to FIG. 12A showing the centering mechanism advanced from the pusher.

In the embodiment of FIGS. 12A, 12B, filter pusher 260 has a proximal portion 262 and a distal portion 264. A centering mechanism 270 is slidingly received within a lumen of the pusher 260 for movement between a retracted position wherein the distal portion of the centering structure is contained within the confines of the pusher 260 in a collapsed position and an extended exposed position (FIG. 12B) wherein the distal portion of the centering structure 270 is exposed from the pusher 260 to move to the expanded position. The centering structure 270 shown includes a series of wires with free ends as in the embodiment of FIG. 5. Alternatively, the centering structure 270 can be in the form of a basket or closed loop as in the structure of FIG. 10A. Actuator 274 moves within elongated slot 265 of hub or handle 266 of pusher 260. The actuator 274 is attached to the centering structure 270 and is moved distally within the slot 265 to advance the centering structure 270 with respect to the pusher 260 and sheath in which the pusher 260 is positioned.

The centering structures described herein are self-expanding, e.g., composed of a shape memory material that automatically returns to the expanded position of FIG. 7A, 10A, 11B or 12B when exposed from the pusher and sheath. It is also contemplated that the structure can be controllably expanded with wires, cable or structure which can be actuated to expand the centering structure. In any of these versions, exposure from the confines of the walls of the pusher and/or sheath enables expansion of the centering structure.

The use of the filter implantation system will now be described. It should be understood that the method of use will be described in conjunction with the centering structure 40 of FIGS. 2-9, it being understood that the centering structure of FIGS. 10A-10C would be utilized in an identical manner. The centering structures of FIGS. 11A-12B would also be used in similar manner, the difference being that the centering structure is slidably attached to the pusher, e.g., via a channel guide or a slot in the hub/handle, as it slides within the pusher lumen rather than being a separate component. Also, the delivery system 10 is shown delivering filter 100 of FIGS. 1 and 2, it being understood that other filters can be delivered with the delivery system of the present application.

In use, once the sheath 20 and dilator (not shown) are inserted through the femoral vein and advanced through the iliac vein into the inferior vena cava, the dilator is removed. Due to the anatomy of the particular patient's vena cava C, the sheath 20 may end up off center such as against the vessel wall V such that distal opening is close to the vessel wall (see FIG. 4). If the filter 100 was then delivered from the sheath 20, it would not be centered on delivery. In accordance with the present invention, the advancement of the centering structure of the present invention moves the distal end 22 and distal opening 24 of the delivery sheath 20 away from a position adjacent or tangent to the vessel wall V so the distal opening 24 of sheath 20 is more centered in the vessel, thus better ensuring the filter 100 will be initially placed in a more centered position.

Figure 4:
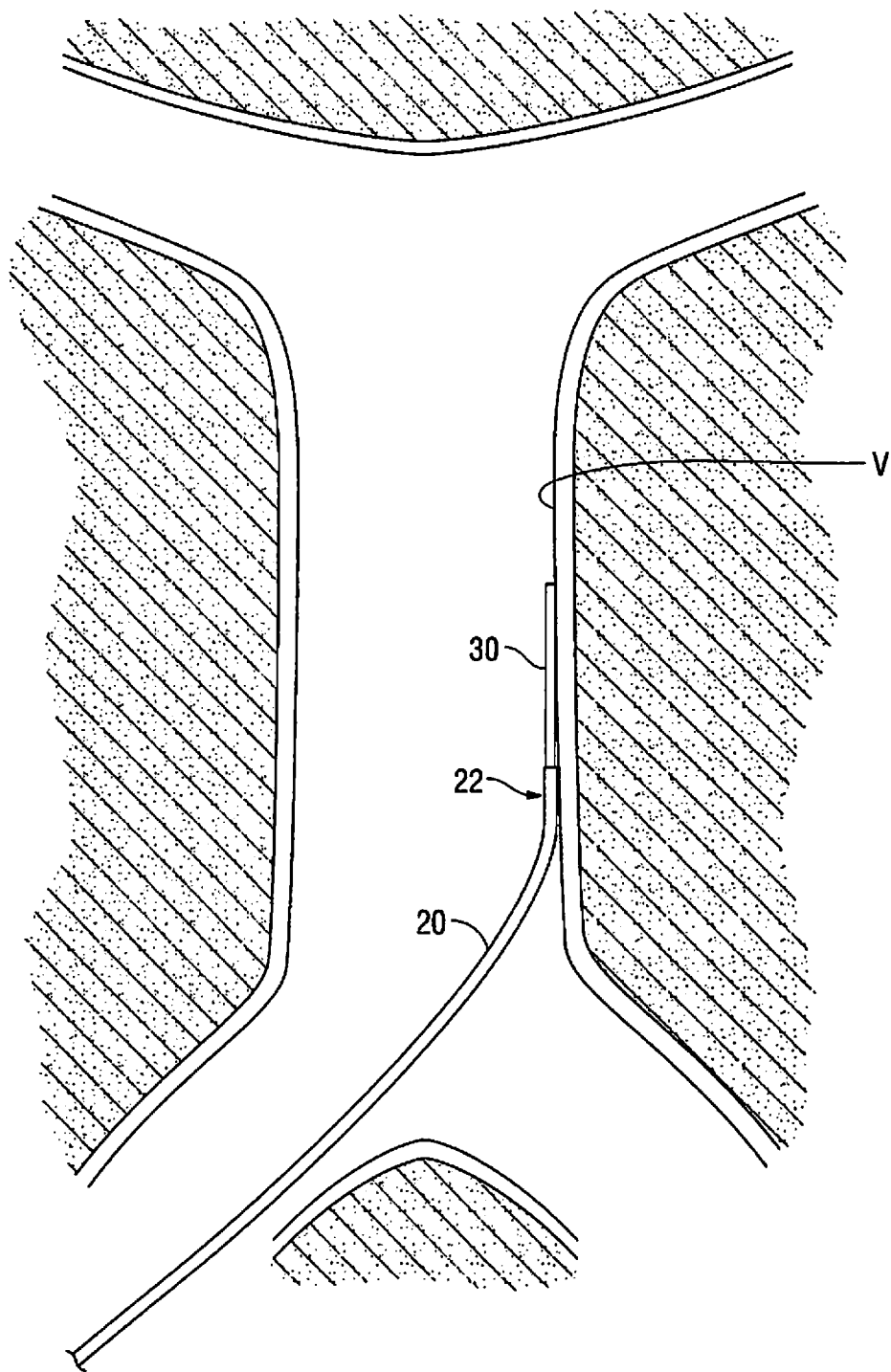
FIG. 4 is a side view of the delivery sheath shown in contact with the wall of the vessel which occurs in certain instances of use, and the filter pusher shown advanced from the catheter.
Figure 13:
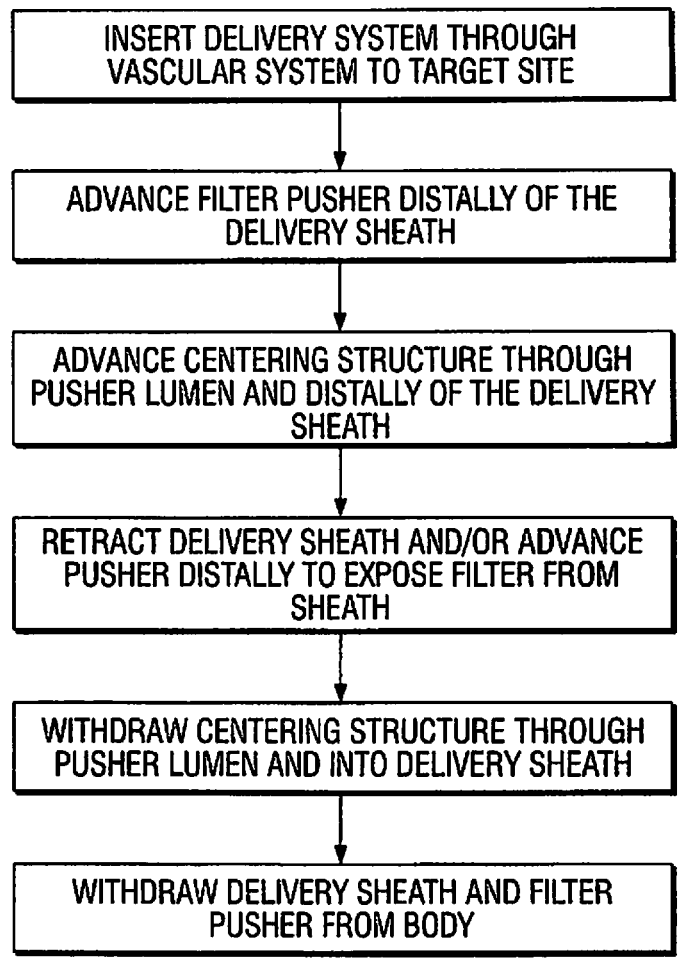
FIG. 13 is a flow chart showing the method steps of the present invention.

Note that during intravascular insertion of the sheath 20 into the vena cava C, filter pusher 30, filter 100 and centering structure 40 positioned therein are fully covered by sheath 20 so as not to be exposed (FIG. 3). With reference to FIGS. 4-9, and to the flow chart of FIG. 13, after the sheath 20 is advanced adjacent the vena cava, the pusher 30 is advanced distally within the delivery sheath 20 to advance the filter 100 distally adjacent a distal end of the sheath 20; however, the filter 100 remains within the delivery sheath 20 with a distal region of the pusher 30 exposed as shown in FIG. 4.

Next, the centering structure 40 is advanced distally from the sheath 20 (FIG. 5), sliding distally within lumen 34 of pusher 30. When the centering arms 44 are exposed from the sheath 20, they move to the expanded configuration as they return to the shape memorized shape. The centering arms 44 ensure the distal opening 24 of sheath 20 is moved away from the vessel wall V, which can be appreciated by comparing FIGS. 4 and 5. In this substantially centered position of the distal tip 22 of sheath 20, the filter 100 is now ready for delivery to the vessel.

The filter 100 is exposed from the sheath 20 (FIG. 6) either by distal advancement of the pusher 30, retraction of the sheath 20, or movement of both the pusher 30 distally and sheath 20 proximally. When the filter 100 is fully exposed (FIG. 7A), it returns to its shape memory position, with the vessel engaging hooks 172 engaging the vessel wall V to secure the filter 100. Note that before fully deployed as in the position of FIG. 6, the user can easily alter the position of placement of the filter 100 by adjusting the longitudinal (i.e., distal or proximal) position by movement of the components.

Figure 8:
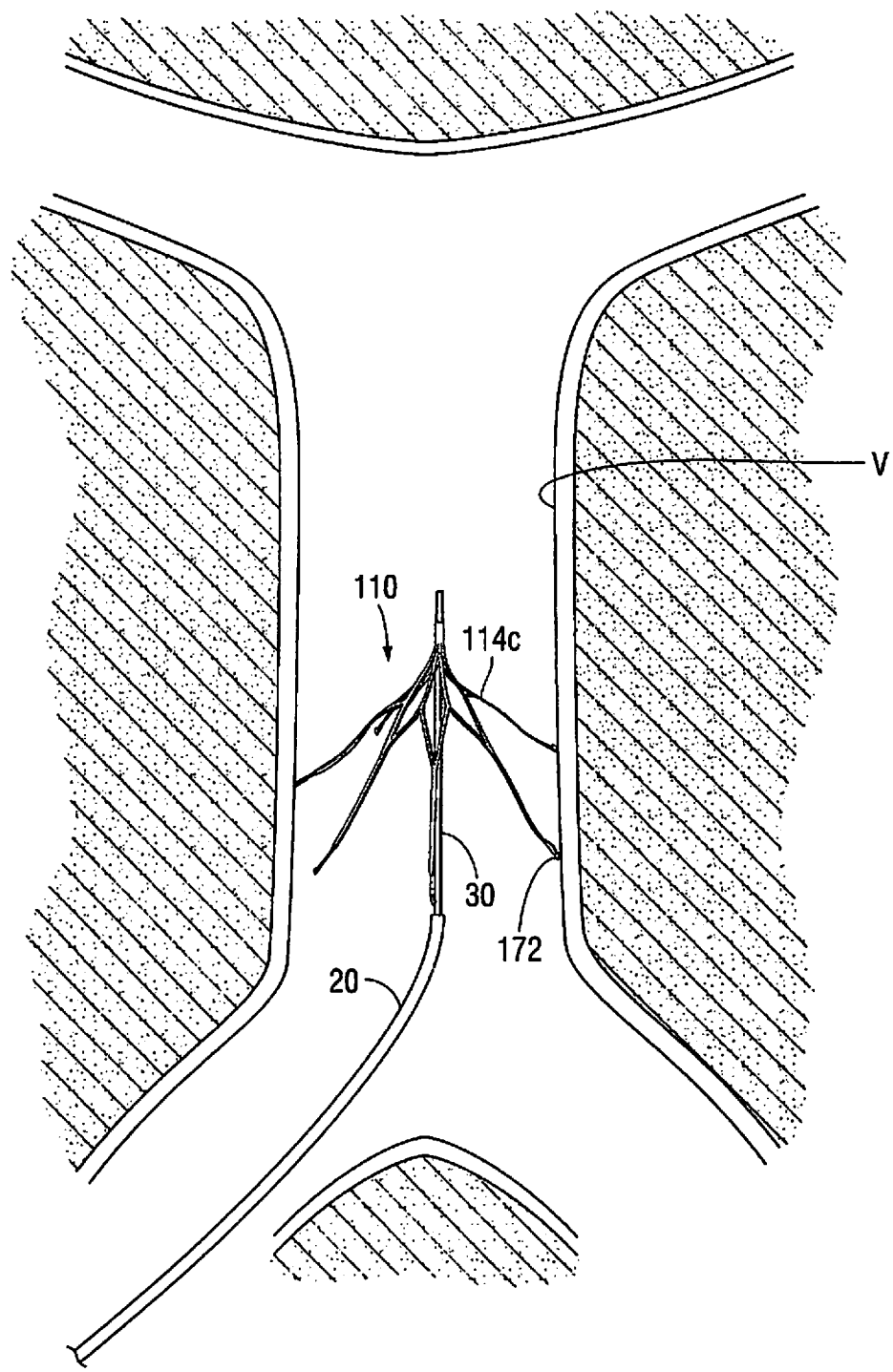
FIG. 8 is a side view similar to FIG. 7B illustrating the centering wires withdrawn into the delivery sheath.

Once the filter 100 is fully deployed in the vessel, the centering structure 40 is then retracted proximally by the user, and the centering arms 44 are thereby collapsed within the lumen 34 of the pusher 30 as it is withdrawn through the pusher 30 and into the sheath 20 (FIG. 8). Once the centering structure 40 is withdrawn, the pusher 30 is retracted proximally within the sheath 20 and the components are removed from the vascular system, leaving the filter 100 in place as shown in FIG. 9.

Note the Figures illustrate filter 100 identical to the filter of U.S. Pat. No. 8,162,972 incorporated by reference above as one example of a filter that can be utilized with the delivery system of the present invention Thus, filter 100 is preferably formed from a single tube, and is preferably composed of shape memory material such as Nitinol. A plurality of cutouts are formed in the filter 100, preferably by laser cutting, although other techniques are contemplated to thereby form struts 114.

Figure 2:
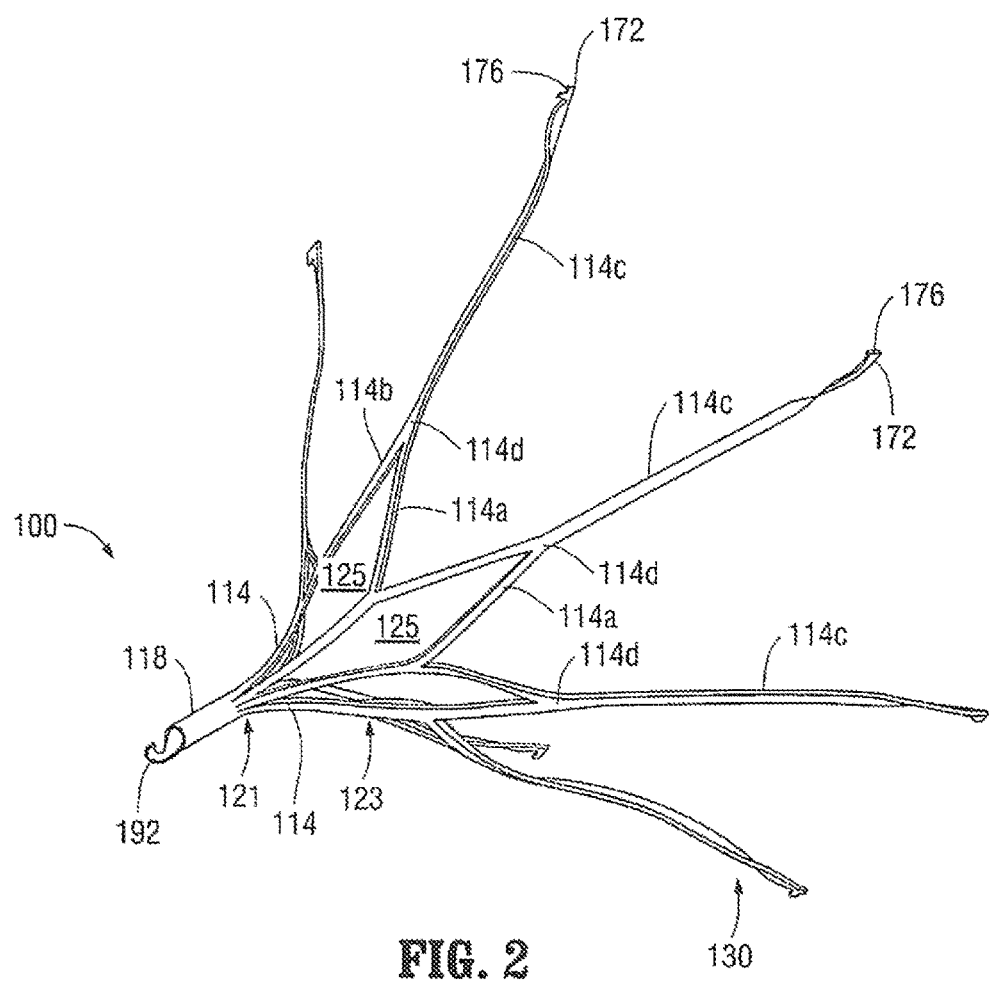
FIG. 2 is a perspective view of the filter of FIG. 1 shown in an expanded position.

Filter 100, as shown in the expanded configuration of FIG. 2, has a filter portion (section) 123 and a mounting portion (section) 130. As shown, filter 100 is generally bell-shaped in configuration. Filter 100 has a flared region and a converging region 121 at the filtering portion 123. The transverse dimension of the filter at the flared (or mounting/anchoring) portion (region) 130 is greater than the transverse dimension at filtering portion (region) 123. Elongated struts 114 are spaced apart as shown and extend at an angle away from the longitudinal axis of the filer 110 to provide a flare.

The struts 114 of filter 1010 terminate in hooks 172. In some embodiments, some struts can terminate in a hook larger than the hook of other struts. In some embodiments, the struts 114 can terminate in alternating larger and smaller hooks such that every other strut 114 would terminate in a small hook and the other struts (in between) would terminate in a larger hook. The penetrating tips 176 of hooks 172 penetrate the tissue to retain the filter, preferably temporarily, and point toward the cranial end of the filter.

The six filter struts or strut portions 114 extend longitudinally and then curve outwardly from tubular portion 118, extend radially therefrom and divide into two connecting filter struts or strut portions 114a, 114b (preferably of equal width, although differing dimensions are contemplated) that angle way from each other (in different directions) to extend to the connecting strut portion of an adjacent strut 114. Thus, connecting strut portion 114a of one strut 114 interconnects with the connecting strut portion 114b of an adjacent strut at joining region 114d. This forms closed geometric shapes 125, preferably substantially diamond shaped in configuration. For clarity, not all of the identical parts are labeled in the drawings.

In the illustrated embodiment, preferably six struts are provided forming twelve interconnecting struts; however a different number of struts and closed geometric shapes can be provided. Note that although all six struts 114 are shown interconnected, it is also contemplated that fewer than all the struts can be interconnected. Also, the strut width can vary as described with respect to the filters disclosed in the '972 patent.

After convergence of strut portions 114a, 114b at joining region 114d, it transitions into elongated mounting strut portions 114c which form the flared mounting or anchoring region 130. The length of the strut portions 114c in the anchoring region 130 can vary, with increased/decreased length increasing the flexibility/rigidity of the struts. The thickness of the strut portions can also vary to affect flexibility/rigidity.

The tubular portion 118 is preferably in the form of a retrieval hook 192. In an alternate embodiment, instead of a retrieval hook 102, a ball or groove can be provided engageable by the retrieval snare (not shown) for retrieval of the filter.

Figure 7C:
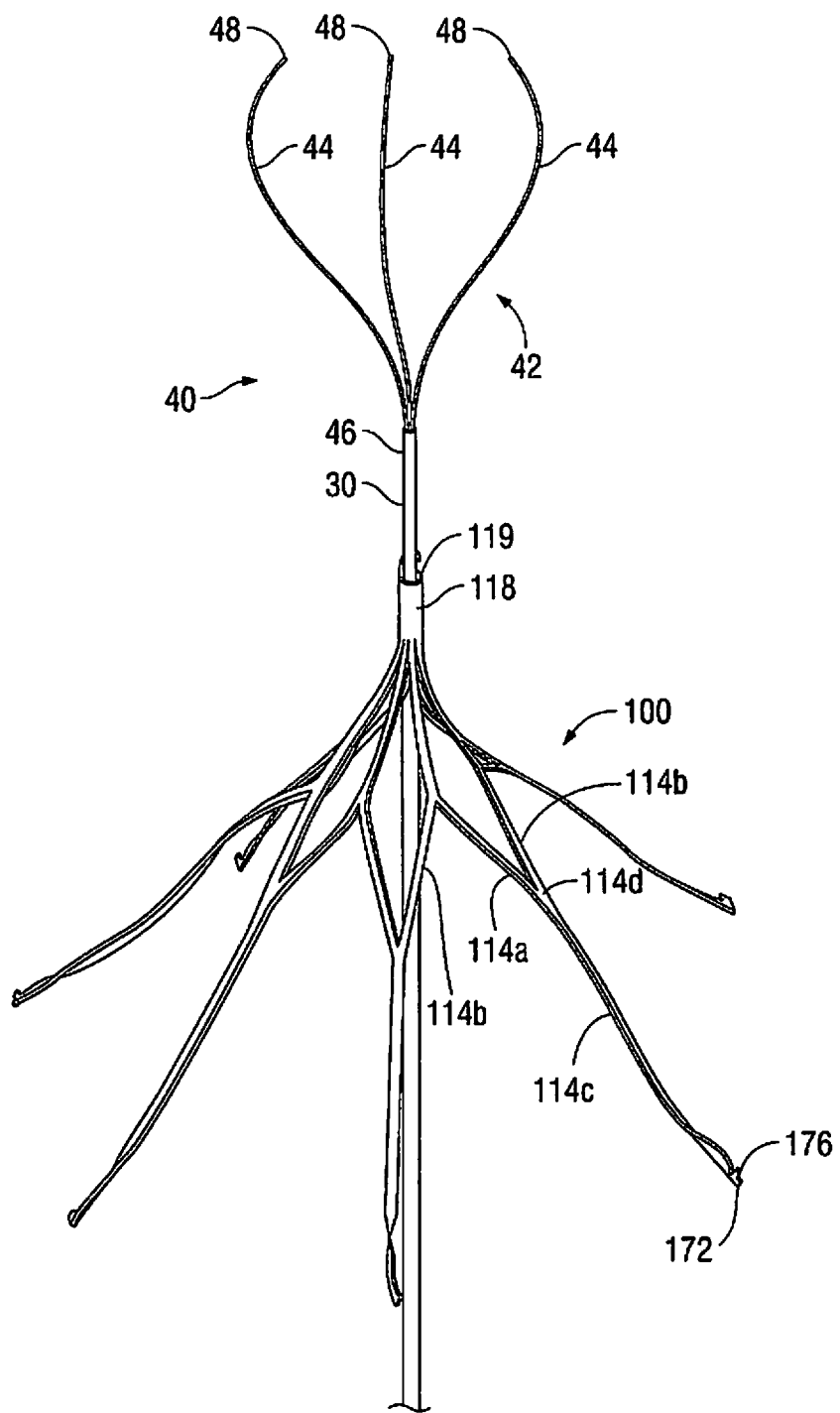
FIG. 7C is an enlarged view of the area of detail designated in FIG. 7A.

Note that the tubular region 118 has a lumen 119 therethrough (see FIG. 7C) through which the filter pusher 30 can extend in the collapsed and in the expanded position of the filter 100. Thus, as shown in FIG. 7C, the centering structure 40 (or 140, 240 or 270), which extends through the pusher 30, would likewise extend through the tubular portion 118. In the collapsed position of the filter of FIG. 1, the pusher 30 would likewise extend through the lumen of the tubular portion 118, and the centering structure 40 (or 140, 240, or 270) would also extend through the lumen 119 of the tubular portion 118.

After exposure of the filter 100 by advancing the pusher 30 to eject the filter 100 or retracting the sheath 20 with the pusher 30 held stationary, or relative movement of both the pusher 30 and sheath 20, the pusher 30 and sheath 20 are removed, enabling the filter 100 to expand from its collapsed position of FIG. 1 and leaving the filter in place in the vena cava.

If it is later desired to remove the filter, the retrieval methods for the filter which are illustrated and described in detail in the '972 patent, such as a retrieval snare, can be utilized.

If the filter 100 is more centered in the vessel, the retrieval snare is better adapted to access and engage (grasp) the retrieval region, e.g., the retrieval hook 192, of the filter 100.

Also, if placement is more centered, removal can be easier because there will be less tissue ingrowth at the retrieval region.

Although described for inserting a vessel filter, the pusher and sheath can be utilized to insert other implants, including vascular implants such as a stent or valve.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An implantation system for a vascular implant comprising:
    a sheath having a longitudinal axis, a lumen formed therein and a distal opening;
    a pusher comprising a lumen and positioned within the sheath, the pusher in contact with the vascular implant to deliver the implant from the sheath, the implant moving from a reduced profile position within the sheath to an expanded placement position outside the sheath, the implant configured for deployment through the distal opening in the sheath for implantation in a patient's body; and
    a sheath centering structure including an elongated portion and a plurality of arms extending from a distal portion of the elongated portion, the sheath centering structure being slidably positioned within the lumen of the pusher, the arms movable from a reduced profile position to an expanded position to move the sheath away from a vessel wall to a more centered position, the centering structure movable relative to the pusher;
    wherein in the collapsed position the plurality of arms are positioned proximally of the distal opening of the sheath and the implant, and in the expanded position the plurality of arms are positioned distally of the distal opening of the sheath and the implant.

2. The system of claim 1, wherein the pusher includes a stepped portion forming a shoulder to support the implant.

3. The system of claim 1, wherein the centering structure is movable independent of the pusher and is movable through the implant.

4. The system of claim 1, wherein the arms of the centering structure are joined at an apex, extend distally from the elongated portion and bow radially outwardly, and terminate in free ends.

5. The system of claim 1, wherein the arms of the centering structure are joined at a proximal apex, extend distally from the elongated portion and bow radially outwardly, and converge at a distal end to form a basket like structure.

6. The system of claim 1, wherein the implant comprises a vessel filter, the filter moving to an expanded configuration when deployed from the sheath.

7. The system of claim 1, wherein the plurality of arms are configured to collapse within the lumen of the pusher when transitioning from the expanded position to the collapsed position.

8. In combination, a delivery sheath, a filter, a pusher and a centering structure, the combination comprising:
    the delivery sheath having a lumen therein dimensioned to receive the filter;
    the filter positioned within the delivery sheath and configured for deployment through a distal opening in the delivery sheath for implantation in a patient's body;
    the pusher comprising a lumen and slidably positioned with respect to the delivery sheath, the pusher engaging the filter for deployment of the filter from the delivery sheath; and
    the centering structure slidably positioned with respect to the filter, pusher and delivery sheath, the centering structure being slidable within the lumen of the pusher, the centering structure having an expandable distal portion to aid centering of the delivery sheath and thus centering of the filter upon delivery from the delivery sheath;
    wherein the expandable distal portion is collapsed when positioned proximally of the distal opening of the delivery sheath and the implant and expanded when positioned distally of the distal opening of the delivery sheath and the implant.

* * * * *